(12) United States Patent
MacDonald et al.

(10) Patent No.: US 10,531,846 B2
(45) Date of Patent: Jan. 14, 2020

(54) POSITRON EMISSION TOMOGRAPHY SYSTEMS FOR USE WITH MAMMOGRAPHY MACHINES AND ASSOCIATED DEVICES AND METHODS

(71) Applicant: University of Washington through its Center for Commercialization, Seattle, WA (US)

(72) Inventors: Lawrence R. MacDonald, Seattle, WA (US); Paul E. Kinahan, Seattle, WA (US)

(73) Assignee: University of Washington, Seattle, WA (US)

( * ) Notice: Subject to any disclaimer, the term of this patent is extended or adjusted under 35 U.S.C. 154(b) by 857 days.

(21) Appl. No.: 14/350,349

(22) PCT Filed: Oct. 24, 2012

(86) PCT No.: PCT/US2012/061715
§ 371 (c)(1),
(2) Date: Apr. 7, 2014

(87) PCT Pub. No.: WO2013/063133
PCT Pub. Date: May 2, 2013

(65) Prior Publication Data
US 2014/0257093 A1    Sep. 11, 2014

Related U.S. Application Data

(60) Provisional application No. 61/550,733, filed on Oct. 24, 2011.

(51) Int. Cl.
*A61B 6/00*          (2006.01)
*A61B 6/03*          (2006.01)
(Continued)

(52) U.S. Cl.
CPC ............ *A61B 6/4275* (2013.01); *A61B 6/037* (2013.01); *A61B 6/0414* (2013.01);
(Continued)

(58) Field of Classification Search
CPC ............ A61B 2017/3411; A61B 6/037; A61B 6/0414; A61B 6/4233; A61B 6/4275;
(Continued)

(56) References Cited

U.S. PATENT DOCUMENTS 5,961,457 A * 10/1999 Raylman ............... A61B 6/4057
                                            250/363.02
7,609,808 B2   10/2009 Tornai et al.
(Continued)

FOREIGN PATENT DOCUMENTS

EP         1529226 B1    11/2011
JP         10502169 A     2/1998
(Continued)

OTHER PUBLICATIONS

Doshi et al. Design and evaluation of an LSO PET detector for breast cancer imaging. Med Phys 27(7):1535-1543, 2000.
(Continued)

*Primary Examiner* — Ruth S Smith
(74) *Attorney, Agent, or Firm* — Perkins Coie LLP (57) ABSTRACT

The present technology describes various embodiments of positron emission tomography (PET) systems for use with mammography machines and associated devices and methods. In several embodiments, a PET system includes a tissue platform and one or more PET detection panels removably coupled to the mammography machine. The panels are configured to generally surround the tissue platform and obtain an approximately 360 degree data sample of tissue. The system can further include an output device configured to output the data sample for image reconstruction. In some
(Continued)

embodiments, the system is configured to provide high resolution images, quantitative image accuracy, dynamic imaging, and/or biopsy guidance.

16 Claims, 5 Drawing Sheets

(51) Int. Cl.
A61B 6/04 (2006.01)
A61B 90/17 (2016.01)
A61B 17/34 (2006.01)

(52) U.S. Cl.
CPC .......... *A61B 6/4233* (2013.01); *A61B 6/4411* (2013.01); *A61B 6/4417* (2013.01); *A61B 6/461* (2013.01); *A61B 6/502* (2013.01); *A61B 6/5235* (2013.01); *A61B 90/17* (2016.02); *A61B 6/508* (2013.01); *A61B 2017/3411* (2013.01)

(58) Field of Classification Search
CPC ..... A61B 6/4411; A61B 6/4417; A61B 6/461; A61B 6/502; A61B 6/508; A61B 6/5235; A61B 90/17
See application file for complete search history.

(56) References Cited

U.S. PATENT DOCUMENTS

| | | |
|---|---|---|
| 8,217,357 B2 | 7/2012 | Stein et al. |
| 2003/0194050 A1 | 10/2003 | Eberhard et al. |
| 2006/0074287 A1 | 4/2006 | Neumann et al. |
| 2006/0239398 A1 | 10/2006 | Mccroskey et al. |
| 2007/0223651 A1 | 9/2007 | Wagenaar et al. |
| 2008/0087833 A1 | 4/2008 | Mccroskey et al. |
| 2008/0103391 A1* | 5/2008 | Dos Santos Varela ............ G01T 1/1615 600/436 |
| 2010/0260316 A1 | 10/2010 | Stein et al. |
| 2010/0261997 A1 | 10/2010 | Ren et al. |
| 2011/0125011 A1 | 5/2011 | Wieczorek et al. |
| 2011/0148861 A1* | 6/2011 | Boellaard ............ G06T 7/0012 345/419 |
| 2012/0068076 A1 | 3/2012 | Daghighian et al. |
| 2012/0101377 A1* | 4/2012 | Hazard ............ G01N 33/57415 600/436 |
| 2012/0114213 A1 | 5/2012 | Buelow et al. |

FOREIGN PATENT DOCUMENTS

| | | |
|---|---|---|
| JP | 2003325499 A | 11/2003 |
| JP | 2005515411 A | 5/2005 |
| JP | 2006511298 A | 4/2006 |
| WO | WO-2007010534 A2 | 1/2007 |
| WO | 2008049773 A2 | 5/2008 |
| WO | 2012049590 A1 | 4/2012 |

OTHER PUBLICATIONS

Adler et al. Method for combined FDG-PET and radiographic imaging of primary breast cancers. Breast 9:163-166, 2003.
Beaulieu et al. SUV varies with time after injection in 18-F-FDG PET of breast cancer: characterization and method to adjust for time differences. J Nucl Med 44(7):1044-1050, 2003.
Bento et al. Architecture and first prototype tests of the clear-PEM electronics system. IEEE NSS Conf Record vol. 6:3796-3800, 2004.
Brasse et al. Fast Fully 3-D Image Reconstruction in PET Using Planograms. IEEE TMI 23(4):413-412, 2004.
Thompson, "Instrumentation for Positron Emission Mammography" (Jan. 2006).
Comtat et al. Simulating whole-body PET scanning with rapid analytical methods. Proc. IEEE NSS/MIC, vol. 3, pp. 1260-1264, 1999.
Daghighian et al. Evaluation of cerium doped lutetium oxyorthosilicate (LSO) scintillation crystals for PET. IEEE TNS 40(4):1045-1047, 1993.
Dahlbom et al. A YSO/LSO phoswich array detector for single and coincidence photon imaging. IEEE Trans. Nucl. Sci. 45(3): 1128-1132, 1998.
Defrise et al. Data acquisition and image reconstruction for 3D PET. The Theory and Practice of 3D PET, vol. 32, Developments in Nuclear Medicine, D. W. Townsend and B. Bendriem, Eds. Dordrecht: Kluwer Academic Publishers, pp. 11-54, 1998.
Derenzo et al. Critical instrumentation issues for <2 mm resolution, high sensitivity brain PET. Quantification of Brain Function. Amsterdam, The Netherlands: Elsevier Science Publishers, pp. 25-37, 1993.
Dobbins JT et al., Digital x-ray tomosynthesis: current state of the art and clinical potential. Phys Med Biol 48:R65-R106 2003.
Dunnwald et al. Residual tumor uptake of [99mTc]-sestamibi after neoadjuvant chemotherapy for locally advanced breast carcinoma predicts survival. Cancer 103(4):680-688, 2005.
Dunnwald et al. Tumor metabolism and blood flow changes by PET : relation to survival in patients with neoadjuvant chemotherapy for locally advanced breast cancer. J Clin Oncol 2008;in press.
Eubank et al. Current and future uses of positron emission tomography in breast cancer imaging. Semin Nucl Med, 34:224-240, 2004.
Hegyesi et al. Development of an FPGA-based data acquisition module for small animal PET. IEEE NSS Conference Record vol. 5:2957-2961, 2004.
Howe et al. Sudbury neutrino observatory neutral current detector acquisition software overview, IEEE Trans Nuc Sci 51(3):878-83, 2004.
Huang, Anatomy of SUV. Nucl Med Biol 27:643-6, 2000.
Huesman et al. List mode maximum likelihood reconstruction applied to positron emission mammography with irregular sampling, IEEE Trans Med Img, 19:532-537, 2000.
Inadama et al. 8-Layer DOI Encoding of 3-Dimensional Crystal Array. IEEE Trans. Nucl. Sci. 53(5): 2523-2528, 2006.
Inadama et al. Performance of 256ch Flat Panel PS-PMT With Small Crystals for a DOI PET Detector. IEEE Trans. Nucl. Sci. 52(1): 15-20, 2005.
Inadama et al. Preliminary evaluation of four-layer BGO DOI-detector for PET. IEEE Trans. Nucl. Sci. 53(1): 30-34, 2006.
Itti et al. Improved scintimammography using a high-resolution camera mounted on an upright mammography gantry. Nucl. Instr. Meth. Phys. Res. A, vol. 497:1-8, 2003.
Kenny et al. Imaging early changes in proliferation at 1 week post chemotherapy: a pilot study in breast cancer patients with 3'-deoxy-3'-[18F]fluorothymidine positron emission tomography. Eur J Nucl Med Mol Imaging 2007;34(9):1339-47.
Kinahan et al. Analytic 3D image reconstruction using all detected events. IEEE Trans. Nucl. Sci., vol. 36, pp. 964-968, 1989.
Laymon et al. Simplified FPGA-Based Data Acquisition System for PET. IEEE Trans. Nucl. Sci., 50(5):1483-1486, 2003.
Lee et al. Detector characteristics of the micro crystal element scanner (MiCES). IEEE TNS 52(5): 1428-1433, 2005.
Lee et al. Impact of system design parameters on image figures of merit for a mouse PET scanner. IEEE TNS 51(1): 27-33, 2004.
Lee et al. Pragmatic fully 3D image reconstruction for the MiCES mouse imaging PET scanner. Phys. Med. Biol. 49:4563-4578, 2004.
Lepage et al. FPGA/DSP-based coincidence unit and data acquisition system for the sherbrooke animal PET scanner. IEEE NSS Conf Record vol. 2:12/173-12/175, 2000.
Levin et al. PSPMT and photodiode designs of a small scintillation camera for imaging malignant breast tumors. IEEE Trans. Nucl. Sci. 44(4): 1513-1520, 1997.
Levine et al. Positron emission mammography: initial clinical results. Ann Surg Oncol 10:86-91, 2003.

(56) References Cited

OTHER PUBLICATIONS

Lewellen et al. A Firewire Based Data Acquisition System for Small Volume Positron Emission Tomographs. 14th IEEE-NPSS Real Time Conference, Stockholm, Sweden, Conf. Record, pp. 260-264, 2005.
Lewellen et al. Initial evaluation of the scintillator LFS for positron emission tomograph applications. Proc IEEE NSS/MIC, vol. 5, pp. 2915-2918, 2004.
Lewellen et al. New Directions for dMiCE—a Depth-of-Interaction Detector Design for PET Scanners. Presented at the 2007 IEEE NSS & MIC, Honolulu, HI, Oct. 29-Nov. 3, 2007.
Lewellen TK, et al. The SimSET Program, in Monte Carlo Calculations in Nuclear Medicine, p. 77-92, M. Ljungberg, S. Strand, and M. King, Editors, Institute of Physics Publishing: Philadelphia, 1998.
Linden et al.: Quantitative Fluoroestradiol Positron Emission Tomography Imaging Predicts Response to Endocrine Treatment. J Clin Oncol 24(18):10.1200/JCO.2005.04.3810 (publ online ahead of print), 2006.
Ling et al. Performance Characteristics of Continuous Miniature Crystal Element (cMiCE) Detectors. IEEE NSS Conference Record vol. 3:1586-1589, 2005.
MacDonald et al. Depth of interaction for PET using segmented crystals. IEEE Trans Nuc Sci 45(4):2144-2148, 1998.
MacDonald et al. Parallax correction in PET using depth of interaction information. IEEE Trans. Nucl. Sci. 45(4): 2232-2237. 1998.
MacDonald et al. Pinhole SPECT of mice using the LumaGEM gamma camera. IEEE Trans. Nucl. Sci. 48(3): 830-836, 2001.
Mankoff et al. Blood flow and metabolism in locally advanced breast cancer: relationship to response to therapy. J Nucl Med 43:500-509, 2002.
Mankoff et al. Analysis of blood clearance and labeled metabolites for the estrogen receptor tracer [F-18]-16!-Fluorestradiol (FES). Nucl Med Biol 24(4):341-348, 1997.
Mankoff et al. Changes in blood flow and metabolism in locally advanced breast cancer treated with neoadjuvant chemotherapy. J Nucl Med 44:1806-1814, 2003.
Mankoff et al. Changes in glucose metabolism and blood flow following chemotherapy for breast cancer. PET Clin 1:71-81, 2005.
Hinse et al. Improving the Spatial Resolution and Image Noise in Densely Pixilated Detectors for Positron Emission Mammography. IEEE Trans. Nucl. Sci. 52(3): 676-683, 2005.
McArthur et al. Advances in adjuvant chemotherapy of early stage breast cancer. Cancer Treat Res. 141:37-53, 2008.
McElroy et al. Evaluation of breast tumor detectability with two dedicated, compact scintillation cameras. IEEE Trans. Nucl. Sci. 49(3): 794-802, 2002.
McElroy et al. Performance evaluation of A-SPECT: a high resolution desktop pinhole SPECT system for imaging small animals. IEEE Trans. Nucl. Sci. 49(5): 2139-2147, 2002.
Melcher et al. Cerium-doped lutetium oxyorthosilicate: a fast, efficient new scintillator. IEEE TNS 39(4):502-505, 1992.
Melcher, Scintillation crystals for PET. J Nucl Med 41(6):1051-1055, 2000.
Missimer et al. Performance evaluation of the 16- module quad-HIDAC small animal PET camera. Phys, Med. Biol. 49:2069-81, 2004.
Miyaoka et al. Optimization of mounting large crystal arrays to photomultiplier tubes. IEEE NSS Conference Record, vol. 3:2039-2042, 2003.
Miyaoka et al. Performance Characteristics of a Second Generation Micro Crystal Element (Mice2) Detector. Proc IEEE NSS pp. 1124-1127, 2001.
Miyaoka et al. Performance characteristics of micro crystal element (MiCE) detectors. IEEE TNS 48(4):1403-1407, 2001.
Mortimer et al. Metabolic Flare: Indicator of Hormone Responsiveness in Advanced Breast Cancer. J Clin Oncol 19(11):2797-2803, 2001.
Moses et al. Instrumentation optimization for positron emission mammography. Nucl Instr Meth A 527:76-82, 2004.
Motta et al. A full Monte Carlo simulation of the YAP-PEM prototype for breast tumor detection. Nucl Instr Meth A 527:201-205, 2004.
Murthy et al. Positron emission mammographic instrument: initial results. Radiology 215:280-285, 2000.
Murthy et al. Results of preliminary clinical trials of the positron emission mammography system PEM-I: a dedicated breast imaging system producing glucose metabolic images using FDG. J Nucl Med 41:1851-1858, 2000.
Oshida et al. Predicting the prognoses of breast carcinoma patients with positron emission tomography using 2-deoxy-2-fluoro[18F]-D-glucose. Cancer 82(11):2227-2234, 2000.
Proffitt et al. A Flexible High-Rate USB2 Data Acquisition System for PET and SPECT Imaging. IEEE NSS Conf Record vol. 5:2971-2975, 2005.
Qi et al. Comparison of rectangular and dual-planar emission mammography scanners. IEEE Trans. Nucl. Sci. 49(5): 2089-96, 2002.
Rajendran et al. Hypoxia and Glucose Metabolism in Malignant Tumors: Evaluation by [18F]Fluoromisonidazole and [18F]Fluorodeoxyglucose Positron Emission Tomography Imaging. Clin. Cancer Res. 10:2245-2252, 2004.
Raylman et al. A Monte-Carlo simulation study of detector array design for dedicated breast metabolic imaging systems. NIMA 555: 403-410, 2005.
Raylman et al. Corrections for the Effects of Accidental Coincidences, Compton Scatter, and Object Size in Positron Emission Mammography (PEM) Imaging. IEEE TNS 48(3):913-923, 2001.
Raylman et al. The potential role of positron emission mammography for detection of breast cancer. A phantom study. Med. Phys. 27(8):1943-1954, 2000.
Ribeiro et al. Breast imaging with a dedicated PEM. Nucl Instr Meth A 527:87-91, 2004.
Rosen et al. Detection of primary breast carcinoma with a dedicated, large-field-of-view FDG PET mammography device: initial experience. Radiology 234:527-534, 2005.
Rouze et al. Design of a Small Animal PET Imaging System with 1 Microliter Volume Resolution. IEEE TNS 51(3):757-763, 2004.
Schelling et al. Positron emission tomography using [18F] fluorodeoxyglucose for monitoring primary chemotherapy in breast cancer. J Clin Oncol 18(8):1689-1695, 2000.
Segars et al. Development of an interactive software application to model patient populations in the 4D NURBS-based cardiac torso phantom. IEEE NSS Conf Record, vol. 3:20/51-20/55, 2000.
Smith et al. Analysis of Factors Affecting Positron Emission Mammography (PEM) Image Formation. IEEE TNS 50(1):53-59, 2003.
Smith et al. PEM-PET Image Reconstruction in a Clinically-Relevant Time Frame. 2006 IEEE Nuclear Science Symposium Conference Record vol. 3:1792-1796, 2006.
Smith et al. Positron emission mammography with tomographic acquisition using dual planar detectors: initial evaluations. Phys. Med. Biol. 49:2437-2452, 2004.
Smith et al. Positron emission tomography using [(18)F]-fluorodeoxy-D-glucose to predict the pathologic response of breast cancer to primary chemotherapy. J Clin Oncol 18(8):1676-1688, 2000.
Sossi et. al. The Second Generation HRRT a Multi-Centre Scanner Performance Investigation. IEEE NSS Conference Record, vol. 4:2195-2199, 2005.
Stafford et al. Use of Serial FDG PET to Measure the Response of Bone-Dominant Breast Cancer to Therapy. Acad Radiology, 9(8):913-921, 2002.
Tafra et al. Pilot clinical trial of 18F-fluorodeoxyglucose positron-emission mammography in the surgical management of breast cancer. Am J Surg 190:628-632, 2005.
Tewson et al. Interactions of 16!-[18F]-fluoroestradiol (FES) with sex steroid binding protein (SBP). Nucl Med Biol 26(8):905-913, 1999.
Thompson et al. Feasibility of positron emission mammography. Med Phys 21:529-538, 1994.
Thompson et al. Positron emission mammography (PEM): a promising technique for detecting breast cancer. IEEE TNS 42(4):1012-1017, 1995.

(56) References Cited

OTHER PUBLICATIONS

Tornai et al. A 3D gantry single photon emission tomograph with hemispherical coverage for dedicated breast imaging. Nucl. Instr. Meth. Phys. Res. A, vol. 497:157-167, 2003.

Tseng et al. 18F-FDG kinetics in locally advanced breast cancer: correlation with tumor blood flow and changes in response to neoadjuvant chemotherapy. J Nucl Med 45:1829-1837, 2004.

Turkington et al. A large field of view positron emission mammography imager. IEEE NSS/MIC Conf. Record vol. 3, pp. 1883-1886, 2002.

Virador et al. Reconstruction in PET cameras with irregular sampling and depth of interaction capability, IEEE Trans. Nucl. Sci. 45(3): 1225-30, 1998.

Wahl et al. Metabolic monitoring of breast cancer chemohormonotherapy using positron emission tomography: initial evaluation. J Clin Oncol 11:2101-2111, 1993.

Wang et al. Characterization of the LBNL PEM Camera. IEEE TNS 53(3):1129-1135, 2006.

Weber et al. Giant birefringent optics in multilayer polymer mirrors. Science 287:2451-6, 2000.

Weber, Use of PET for monitoring cancer therapy and for predicting outcome. J Nucl Med 46(6):983-995, 2005.

Weinberg et al. Applications of a PET device with 1.5 mm FWHM intrinsic spatial resolution to breast cancer imaging. Conf Proc IEEE Internatl Symp Biomed Img: Macro to Nano, vol. 2:1396-1399, 2004.

Weinberg et al. Preliminary results for positron emission mammography: real-time functional breast imaging in a conventional mammographic gantry. Eur J Nucl Med 23:804-806, 1996.

Wu T et al., Tomographic mammography using a limited number of low-dose cone-beam projection images. Med. Phys. 30(3):365-380, 2003.

Zhang et al. A Prototype Modular Detector Design for High Resolution Positron Emission Mammography Imaging. IEEE Trans. Nucl. Sci. 50(5): 1624-1629, 2003.

International Search Report and Written Opinion dated Jan. 31, 2013 in International Application No. PCT/US2012/061715 filed Oct. 24, 2012. 14 pages.

Christopher J. Thompson, "Instrumentation for Positron Emission Mammography", Pet Clinics, WB Saunders Co, US. vol. 1, No. 1, Jan. 1, 2006. pp. 33-38.

Office Action dated Aug. 30, 2016 in Japan Application No. 2014-538937, 9 pages.

\* cited by examiner

POSITRON EMISSION TOMOGRAPHY SYSTEMS FOR USE WITH MAMMOGRAPHY MACHINES AND ASSOCIATED DEVICES AND METHODS

CROSS-REFERENCE TO RELATED APPLICATION(S)

This application is a U.S. national phase application based on International Application No. PCT/US2012/061715, filed on Oct. 24, 2012, which claims the benefit of U.S. Provisional Patent Application No. 61/550,733, filed on Oct. 24, 2011, each of which is incorporated herein by reference in its entirety.

STATEMENT OF GOVERNMENT INTEREST

This invention was made with government support under CA134855 awarded by the National Institutes of Health. The government has certain rights in the invention.

TECHNICAL FIELD

The present technology is generally directed to positron emission tomography systems for use with mammography machines and associated devices and methods. More specifically, some embodiments are directed to systems providing high resolution images, quantitative image accuracy, dynamic imaging, and/or biopsy guidance.

BACKGROUND

Breast cancer is a common malignancy among women. Early detection by screening mammography and an increasing array of treatment options have recently been successful in reducing breast cancer mortality. As both detection and systemic treatment of breast cancer continue to advance, lesion characterization is becoming increasingly important for determining appropriate therapy. Selection of the correct therapy can maximize treatment efficacy while minimizing treatment-related morbidity. There is an important need to characterize early breast cancers, especially their aggressiveness, to match the intensity of the treatment approach to the likelihood the tumor will recur or spread systemically. Furthermore, characterizing tumor biology helps identify appropriate targets for systemic therapy. Additionally, early response assessment can identify treatments likely to be ineffective, and direct alternate choices for treatment.

While positron emission tomography (PET) is increasingly used for advanced breast cancer, it has been less useful in early-stage breast cancer that presents as a smaller lesion in the breast. This is in part due to the limited spatial resolution offered by whole-body PET scanners. Accordingly, there exists a need for improved breast lesion imaging and characterization.

DETAILED DESCRIPTION

The present technology describes various embodiments of PET systems for use with mammography machines and associated devices and methods. In several embodiments, a PET system includes a tissue platform and one or more PET detection panels removably coupled to the mammography machine. The panels are configured to generally surround the tissue platform and obtain an approximately 360 degree data sample of tissue. The system can further include an output device configured to output the data sample for image reconstruction. In some embodiments, the system is configured to provide high resolution images, quantitative image accuracy, dynamic imaging, and/or biopsy guidance.

Specific details of several embodiments of the technology are described below with reference to FIGS. 1-4. Other details describing well-known structures and systems often associated with mammography and PET have not been set forth in the following disclosure to avoid unnecessarily obscuring the description of the various embodiments of the technology. Many of the details, dimensions, angles, and other features shown in the Figures are merely illustrative of particular embodiments of the technology. Accordingly, other embodiments can have other details, dimensions, angles, and features without departing from the spirit or scope of the present technology. A person of ordinary skill in the art, therefore, will accordingly understand that the technology may have other embodiments with additional elements, or the technology may have other embodiments without several of the features shown and described below with reference to FIGS. 1-4.

Figure 1:
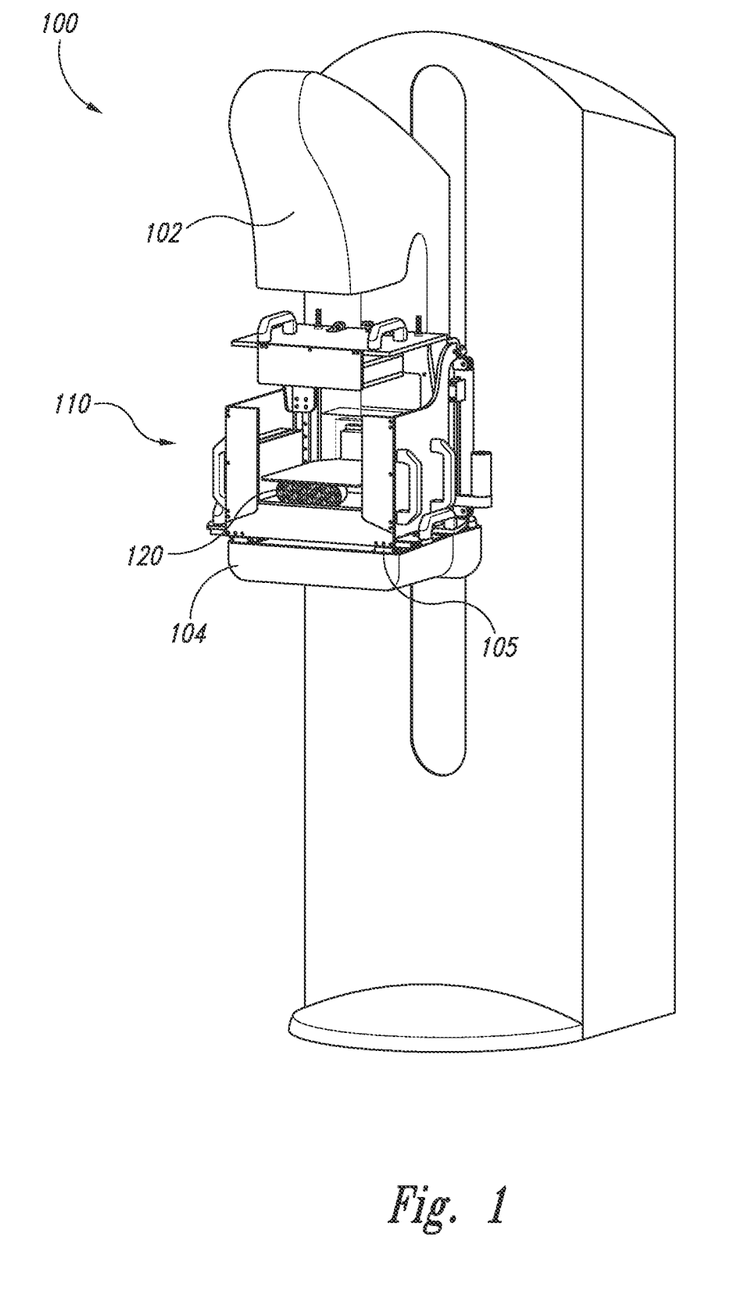
FIG. 1 is an isometric view of a mammography machine having a PET system incorporated therein and configured in accordance with embodiments of the technology.

FIG. 1 is an isometric view of a mammography machine 100 having a PET system 110 incorporated therein and configured in accordance with embodiments of the technology. The mammography machine 100 can be any type of mammography device known in the art and can include features typical of mammography devices. For example, in the illustrated embodiment of an upright mammography machine 100, the mammography machine 100 includes an x-ray tube housing 102 and an x-ray detector platform 104. In traditional use, a patient can position her breast (represented by compressed saline bag 120) between the platform 104 and a compression paddle configured to compress the breast tissue against the platform 104 for improved imaging. In further embodiments, the PET system 110 can be integrated with other standard or tomosynthesis mammography devices. In some embodiments, the PET system 110 is electrically integrated with the mammography machine 100, and the mammography machine 100 and PET system 110 can provide integrated data output for imaging or other processing.

In various embodiments, the PET system 110 can be removably or permanently coupled to the mammography machine 100 or can be manufactured as an integral component of the mammography machine 100. In the illustrated embodiment, the PET system 110 is positioned on the platform 104. In some embodiments, the PET system 110 can be attached to the mammoaraphy machine at one or more rails 105 traditionally used to attach anti-scatter grids and/or magnification platforms. The PET system 110 can be configured to fit in an existing mammography machine 100 to form a dual-modality unit within the footprint of a traditional mammography suite.

As with traditional PET systems, the PET system 110 utilizes a nuclear medicine imaging technique that produces a three-dimensional image or picture of functional processes in the body. The system 110 detects pairs of annihilation photons emitted indirectly by a positron-emitting radionuclide (tracer), which is introduced into the body on a biologically active molecule. Three-dimensional images of tracer concentration within the body are then constructed by computer analysis. In some embodiments, the three-dimensional imaging is accomplished with the aid of an X-ray scan performed on the patient by the mammography machine (or other device, such as tomosynthesis) during the same session. The concentrations of tracer imaged provide information related to the biological target of the tracer. For example, the radiotracer 18-F-fluorodeoxyglucose (FDG) reveals information about tissue metabolic activity (representative of the possibility of the presence of cancer).

In some embodiments, the biologically active molecule chosen for PET is 18-F-fluorodeoxyglucose (FDG), an analogue of glucose. FDG and other PET tracers can be used to characterize breast cancer and measure response to treatment. Primary tumor uptake of FDG can be predictive of survival and response. For example, as will be described in further detail below with reference to FIG. 4, serial FDG analysis can be effective in measuring response to systemic therapy, including early in the course of therapy. Tracers other than FDG can be used to characterize breast cancer and identify targets for systemic treatment. For example, using 18-F-fluoroestradiol, a user can perform an in vivo assessment of estrogen receptor expression and function, which predicts response to endocrine therapy and early assessment of response. Other PET tracers can be used to assess angiogenesis, cell proliferation, epidermal growth factor receptor-2 (ErbB-2 or HER-2) expression, and apoptosis, and offer new methods for evaluating and characterizing breast carcinoma. In still further embodiments, many other radiotracers can be used by the PET system 110 to image the tissue concentration of molecules of interest. Unlike in vitro assays, performed on small tissue samples, PET imaging with targeted agents can allow in vivo assessment of target expression and distribution within the tumor.

By measuring tracer uptake, the PET system 110 can be used to provide a quantitative assessment of response to systemic therapy. In some embodiments, as will be described in further detail below with reference to FIGS. 2A and 2B, complete tomographic data sampling and quantitative imaging can be accomplished in an imaging volume appropriate for a compressed breast by positioning PET detector panels substantially around the breast.

Figure 2A:
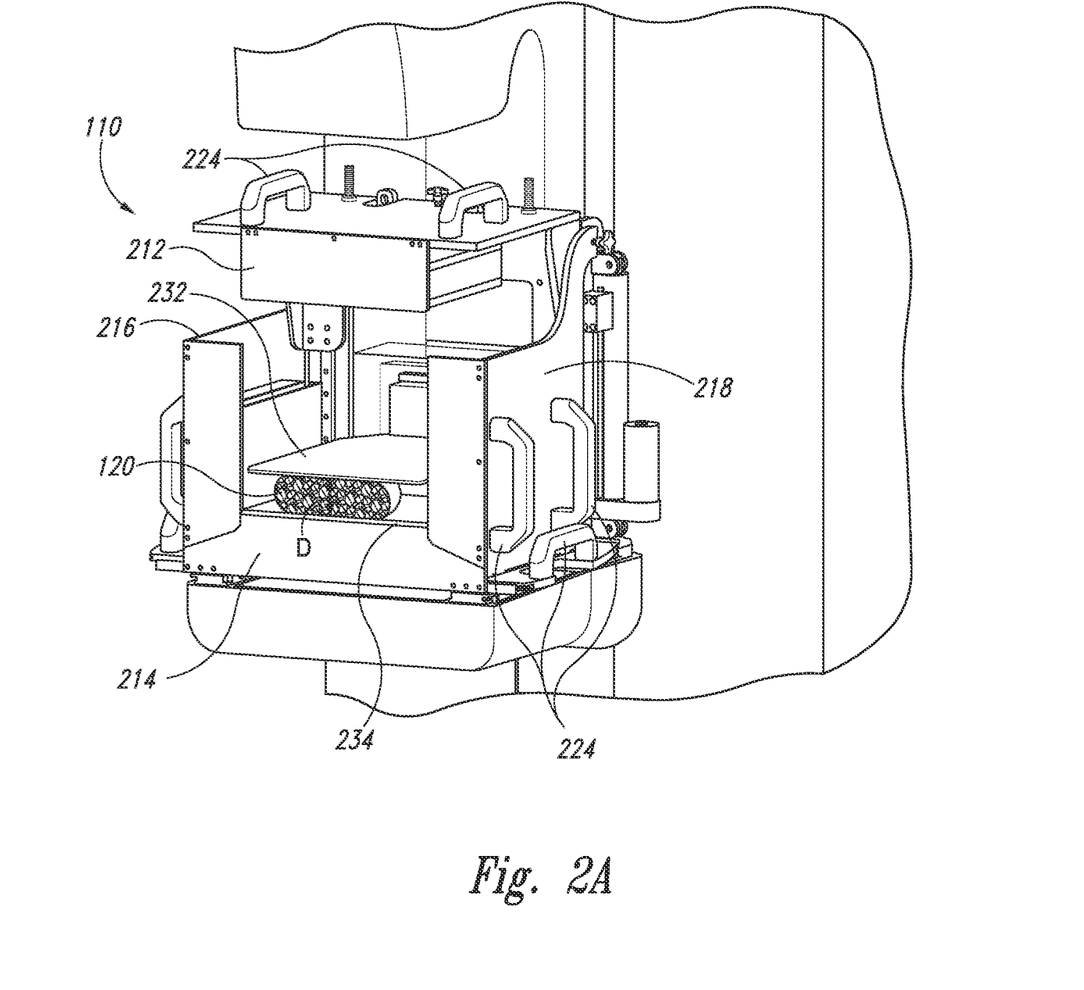
FIG. 2A is an isometric view of the PET system arranged in an uncompressed configuration in accordance with embodiments of the technology.
Figure 2B:
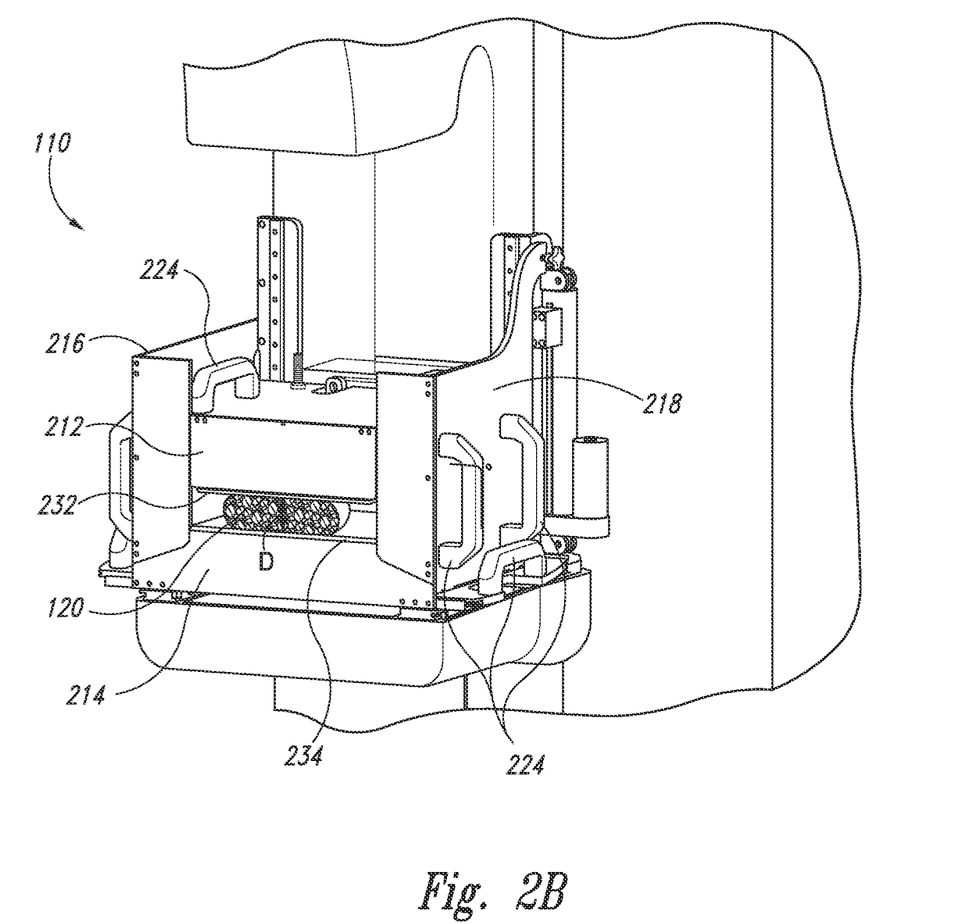
FIG. 2B is an isometric view of the PET system of FIG. 2A arranged in a compressed configuration in accordance with embodiments of the technology.

FIG. 2A is an isometric view of the PET system 110 arranged in an uncompressed configuration in accordance with embodiments of the technology. FIG. 2B is an isometric view of the PET system 110 arranged in a compressed configuration in accordance with embodiments of the technology. Referring to FIGS. 2A and 2B together, the PET system 110 comprises a top detector panel 212, a bottom detector panel 214, and first and second side detector panels 216, 218 positioned generally orthogonal to the top and bottom panels. In some embodiments, the top and bottom panels 212, 214 have scanning dimensions of 20×15 cm and the side panels 216, 218 have scanning dimensions of 10×15 cm. These panels 212-218 collectively form a field of view (FOV) of 20 cm×15 cm×variable separation, D. The panels can have other dimensions in other embodiments. In still further embodiments, the PET system 110 comprises shapes or configurations other than top, bottom, and side panels. For example, in some embodiments, the PET system 110 comprises a cylindrical or partially cylindrical shape configured to radially surround a breast. In further embodiments, the PET system 110 can comprise other shapes (e.g., a square, clamshell, etc.) allowing for a scan of approximately 360 degrees for a "ring") around the breast 120.

In the illustrated embodiment, the panels 212-218 comprise flat panel detectors constructed from scintillation crystals and position-sensitive photo-sensors or photomultiplier tubes. The scintillation crystals can be optimized to provide the desired spatial sampling and gamma ray absorption sensitivity. For example, the detectors can comprise one or more layers of crystals, Wherein different layers can comprise the same or different crystal lengths or widths. These crystal dimensions may also vary within an individual layer. In some embodiments, crystals in the top and bottom panels 214, 216 have crystal lengths of approximately 10-20 mm, while crystals in the side panels have crystal lengths of approximately 10, 20, 30, 40, or 50 mm. In some embodiments. different crystal lengths can be selected to normalize imaging sensitivity. The crystals can comprise lutetium oxyorthosilicate or other suitable materials. In some embodiments, solid-state (silicon) photomultipliers are used in place of position-sensitive photomultiplier tubes.

In operation, the breast 120 can be held in place or immobilized by a superior immobilization panel 232 and an inferior immobilization panel 234. The superior and inferior panels 232, 234 can be part of the mammography machine, part of the PET system 110, or separate components altogether. In several embodiments, the breast 120 need not be compressed for PET system 110 operation, so the superior panel 232 can be relatively lightweight and can stay in place for several (e.g., three to five) minutes without causing the patient discomfort. In still further embodiments, the breast 120 can be immobilized by the top and bottom panels 214, 216 and the superior and inferior panels 232, 234 can be absent. As will be discussed in further detail below with reference to FIG. 3, the top panel 214 can be lowered from an open configuration (FIG. 2A) to a compressed configuration (FIG. 2B) where the top panel 214 is adjacent to the breast 120 or adjacent to the superior immobilization panel 232. The panels 212-218 can include handles 224 configured to allow an operator to lift and place the panels in position for imaging. In several embodiments, the PET imaging is performed either before or after the mammography imaging, with the detector panels 212-218 inserted or removed as appropriate, While the immobilization panels 232, 234 can keep the patient in the same position for both types of imaging. The immobilization panels 232, 234 can inhibit patient motion between mammogram and PET imaging. In further embodiments, the PET and mammogram imaging are done at different times. While the illustrated embodiment includes handles 224 for mechanical placement by an operator, in further embodiments the panels 212-218 can be placed by machine operation. In some embodiments, each of the detection panels 212-218 can be placed individually on the mammography machine prior to use. In further embodiments, one or more of the detection panels 212 are coupled together during placement on the mammography machine.

Figure 2C:
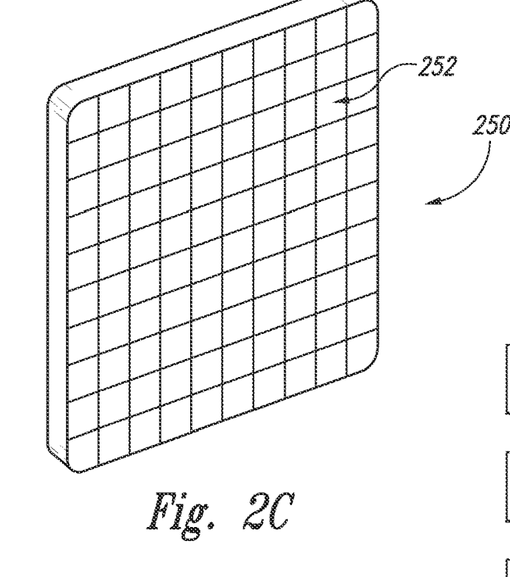
FIG. 2C is an isometric view of a biopsy grid configured for use with the PET system of FIGS. 2A and 2B in accordance with embodiments of the technology.

FIG. 2C is an isometric view of a biopsy grid 250 configured for use with the PET system 110. Referring to FIGS. 2A-2C together, in some embodiments, one or more of the detection panels (e.g., one or both of the side panels 216, 218) include or are interchangeable with the biopsy guidance grid 250. The biopsy guidance grid 250 can be used to guide a biopsy needle based on imaging results. In a particular embodiment, for example, the imaging results can indicate a particular portion of a tumor that should be extracted for further evaluation. A biopsy needle can enter an exact position of the breast 120 by aligning with and traversing through a particular aperture 252 in the grid 250. In further embodiments, the biopsy grid 250 can be used in conjunction with an x-ray mammography machine.

Figure 3:
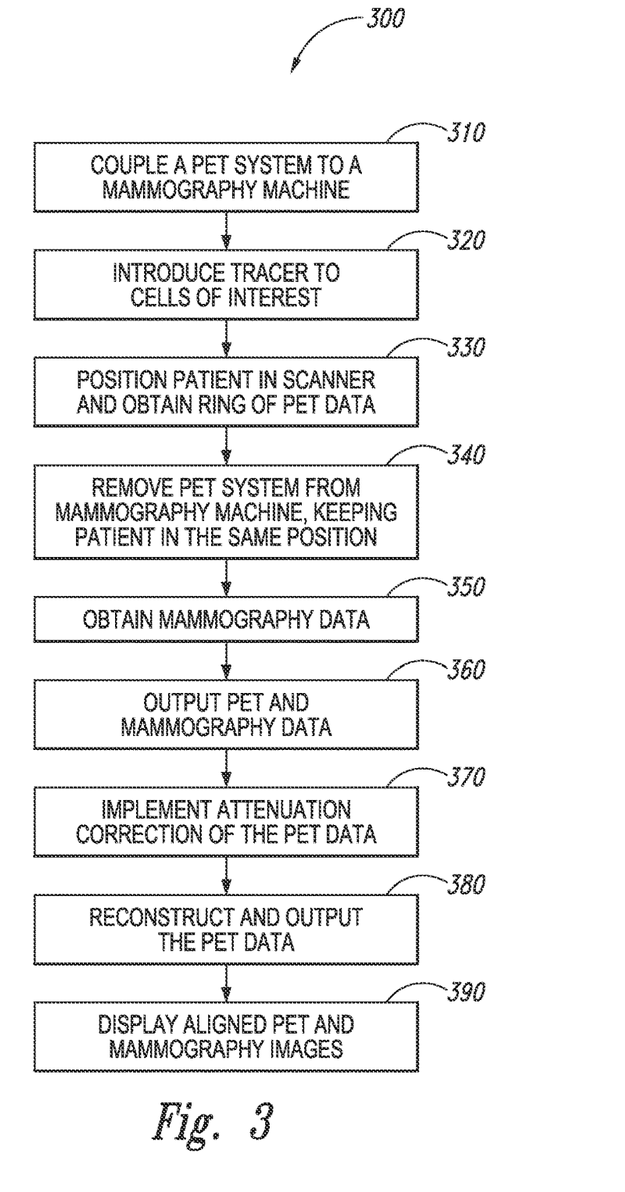
FIG. 3 is a block diagram illustrating a method of using the PET system.

FIG. 3 is a block diagram illustrating a method 300 of using the PET system. The method 300 includes coupling a PET system to a mammography or tomosynthesis machine, 310. As discussed above, the PET system can be removably coupled to an existing mammography machine, and does not necessarily require a dedicated machine. The method 300 includes introducing a radiotracer, such as FDG, to cells of interest 320 (e.g., breast cells). The tracer can be introduced to the patient in advance of imaging or during imaging. The method 300 further includes positioning a patient in the PET system and obtaining a ring of PET data from the breast 330. The approximately 360 degree "ring" of data can be obtained from an arrangement of PET panels that surround or substantially surround the breast tissue. In further embodiments, only a partial "ring" of data can be obtained. In further embodiments, the data is obtained as a function of time, so a dynamic "movie" of tracer uptake can be created. The method 300 can further include removing the PET system from the mammography or tomosynthesis machine, while keeping the patient in the same position 340. The method 300 can include obtaining mammography or tomosynthesis data 350. In further embodiments, the PET and mammography data can be obtained in the opposite order, or only one type of data can be collected.

The PET and mammography or tomosynthesis data are output to a processing system 360. The processing system can be integral to or externally coupled to or in communication with the PET system and/or mammography machine. The processing system can measure the amount of tracer uptake and/or prepare the PET data for useful output. In some embodiments, the PET system 110 can utilize high-speed readout electronics (e.g., having count rate capabilities at or above 800 kcps). With high count-rate capability, the PET system 110 can image higher injected tracer doses with reduced imaging time and/or higher image statistics.

Attenuation correction can be implemented on the PET data 370. Accurate attenuation correction is possible on a dual modality PET/mammography system by relying on the constraints that materials behave like water at 511 KeV, and that breast geometry can be used to estimate attenuation, More specifically, a user can utilize the known geometry of the mammogram acquisition, which compresses breast tissue between parallel plates with a known separation. Although photon absorption varies strongly by tissue type at the x-ray mammography energies of 25 to 49 kVp, at the PET photon energy of 511 keV, all soft tissues can allow for essentially identical absorption. The 511 keV attenuation image can thus be built from the three components: the outline of the compressed tissue, the constant thickness of the tissue, and the attenuation of soft tissue at 511 keV. Alternatively, a three-dimensional attenuation map that characterizes spatially variant breast tissue attenuation coefficients at 511 keV can be measured with x-ray tomosynthesis methods, and this can be used for PET attenuation correction. In some embodiments, the outline of the compressed tissue can be obtained from the mammogram acquisition and/or the PET image reconstructed without attenuation correction.

Second-order corrections can compensate for geometrical distortion from one beam geometry, distortion of the compression paddle, and embodiments where the x-ray thickness is less than the separation of the top and bottom PET detection panels. In some embodiments, in cases where non-biological materials are present, e.g. implants, improved accuracy can be achieved through the use of two sequential mammogram acquisitions at different energies, e.g. 25 and 49 kVp. In some embodiments, PET detector proximity in the system results in high geometric sensitivity, but also in oblique lines of response (LOR) that can cause event mispositioning due to parallax if depth-of-interaction (DOI) is not known. Statistics-based event positioning in monolithic crystals can provide high spatial resolution, including DOI, with resolution improving for thinner crystals. Using Monte Carlo simulation, a user can estimate sensitivity and LOR mispositioning due to lack of DOI. Photon sensitivity, scatter fraction (SF), and parallax error can be studied as a function of crystal thickness.

The method 300 further includes reconstructing and outputting the corrected PET data 380. The method 300 can also include displaying aligned PET and mammography images 390. The PET and mammography images can be displayed together on a single output (e.g., a monitor). In further embodiments, only one of the PET or mammography images is displayed.

The PET system can provide high spatial resolution images. For example, the PET system 110 can utilize a high-resolution and high-sensitivity detector geometry that enables quantitative PET imaging. In several embodiments, the PET system can provide a spatial resolution of 1-4 mm, and can achieve quantitative accuracy for objects larger than approximately 5 mm. In other embodiments, other spatial resolutions are achieved. Based on the output image/data, further treatment or evaluation tests can be implemented. For example, additional imaging can be performed or a biopsy can be taken (e.g., using the biopsy guidance system described above). In several embodiments, a biopsy can be facilitated by removal of one or more of the PET detector panels.

Figure 4:
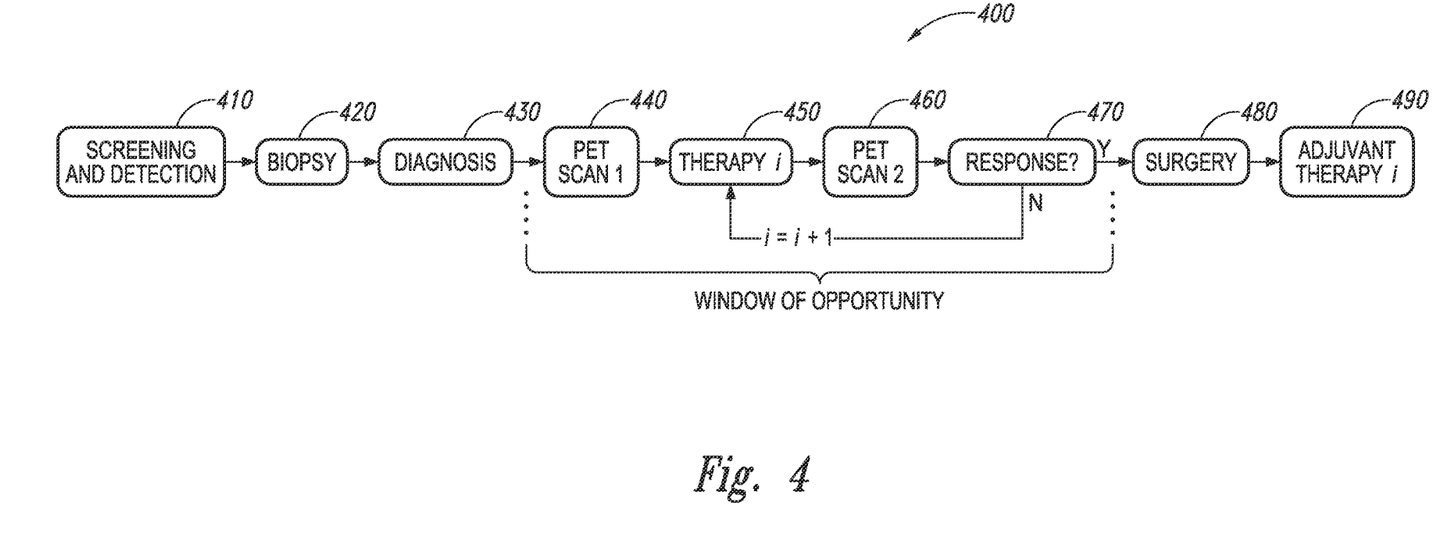
FIG. 4 is a block diagram illustrating a method of implementing serial imaging using the PET system.

FIG. 4 is a block diagram illustrating a method 400 of implementing serial imaging using the PET system. In several embodiments, serial imaging can be facilitated by comparing the alignment of the mammography or tomosynthesis images acquired in serial scans. This alignment information can then be used to align the serial PET images. As discussed above, in several scenarios, the PET system 110 can be used after the presence of cancer has been confirmed to evaluate response to therapy, e.g., in the neoadjuvant setting. As illustrated in FIG. 4, for example, the method 400 can include screening and detecting cancer or other disease 410. This may include a biopsy 420 to make a definitive determination of cancer type.

In some treatment scenarios, it will be cost-effective to measure tracer uptake in known breast cancer for treatment response characterization. A "window of opportunity" is the time (typically a few weeks or months) between a confirmed diagnosis 430 and breast cancer surgery 480 and/or adjuvant therapy 490. The patient can undergo FDG PET at two or more time points during the course of treatment (e.g., estrogen-inhibiting therapies). For example, a pre-therapy scan 440 serves as a. baseline. A post-therapy PET 460 scan is performed at a later time points during or after the course of therapy 450. These serial evaluations demonstrate a significant difference between responders and non-responders 470, and show that tumors responding to neoadjuvant chemotherapy typically demonstrate a decline in tumor FDG uptake at mid-therapy compared to pre-therapy. PET can accordingly be an early predictor of therapy response. Serial PET imaging may therefore serve as not only a clinically useful classifier of response, but may also be a biomarker for improved survival, More specifically, there is an important need to characterize early breast cancers, especially their aggressiveness, to match the intensity of the treatment approach to the likelihood the tumor will recur or spread systemically. Furthermore, characterizing tumor biology can help identify appropriate targets for systemic therapy. Finally, early response assessment can identify treatments likely to be ineffective, and direct alternate choices for treatment.

EXAMPLES

1. A positron emission tomography (PET) system for use with a mammography machine, the system comprising:
   a tissue platform;
   one or more PET detection panels removably coupled to the mammography machine, wherein the panels are configured to generally surround the tissue platform and obtain an approximately 360 degree data sample of tissue; and
   an output device configured to output the data sample for image reconstruction.

2. The PET system of example I wherein the PET detection panels comprise a top panel, a bottom panel, and a plurality of side panels positioned generally orthogonal to the top and bottom panels.

3. The PET system of example 2 wherein the individual panels are movable and separable from one another.

4. The PET system of example 1, further comprising a biopsy guidance grid configured for interchangeable placement with the panel.

5. The PET system of example I wherein the detection panel is configured to obtain a data sample corresponding to a reconstructed image having a spatial resolution of 1-4 mm.

6. The PET system of example I wherein the detection panel is configured to obtain a data sample indicating a quantity of tracer uptake.

7. The PET system of example l wherein the output device is configured to output the data sample in combination with x-ray data.

8. The PET system of example 1 wherein the detection panel is configured to obtain a data sample as a function of time.

9. A positron emission tomography (PET) device configured for attachment to a mammography machine, the PET device comprising:
   a superior detection panel;
   an inferior detection panel opposite the superior detection panel and configured o support tissue for scanning, and
   a plurality of side detection panels generally orthogonal to the superior and inferior detection panels, wherein the superior, inferior, and side detection panels placed together generally surround the tissue.

10. The PET device of example 9, further comprising a biopsy guidance grid configured for interchangeable placement with a side detection panel.

11. The PET system of example 9 wherein at least one of the detection panels includes one or more handles.

12. The PET system of example 9 wherein at least one of the detection panels is configured for removable coupling to a rail system on the mammogram machine.

13. A method of using PET, comprising:
   removably coupling a PET detection panel to a mammography machine;
   obtaining a 360 degree data sample of tissue; and
   reconstructing an image based on the data sample.

14. The method of example 13, further comprising directing tissue sampling in response to the reconstructing.

15. The method of example 13,further comprising quantifying tracer uptake in the tissue.

16. The method of example 15, further comprising relating a quantity of tracer uptake to a structural abnormality of the tissue.

17, The method of example 13, wherein reconstructing the image comprises combining generating an image by combining the data sample with x-ray data.

18. The method of example 13 wherein reconstructing an image based on the data sample comprises generating an image having a spatial resolution of about 1-4 mm.

19. The method of example 13 wherein obtaining a 360 degree data sample of tissue comprises dynamically acquiring a PET image as a function of time.

20. The method of example 13 wherein obtaining a 360 degree data sample of tissue comprises obtaining a baseline data sample, and wherein the method further comprises:
   implementing a treatment on a patient; and
   obtaining a post-therapy data sample.

21. The method of example 13, further comprising correcting attenuation of the image through the use of x-ray mammography data.

The systems and methods described herein offer several advantages over traditional mammography systems. As noted above, the application of PET with FDG to smaller tumors and early stage disease has been limited due to the limitations of whole body scanners for identifying and quantifying tracer uptake in such lesions. Using high-resolution images, the PET systems disclosed herein can evaluate breast cancer characteristics that can guide selection of effective therapies, eliminate ineffective therapies, and measure response to therapies via absolute metrics. This can improve patient outcomes and decrease treatment costs.

The PET systems disclosed herein further provide quantitative accuracy, as the PET images represent an absolute measure of the concentration of PET tracer injection in the tumor (or anywhere in the image). Another advantage of the PET systems disclosed herein is the biopsy guidance capability. Using biopsy guidance in conjunction with high-resolution PET image improves biopsy location accuracy. The PET systems disclosed herein can further include registration with anatomical imaging. The PET image can be spatially registered and fused with an x-ray image (e.g., a standard planar mammogram or pseudo-3D tomosynthesis), The PET systems can further include dynamic imaging, or acquiring a PET image as a function of time, so a user can make a "movie" of the PET tracer distribution from the injection time point onward. Traditional PET tracers are injected, and a practitioner must wait for systematic distribution throughout the patient, when a 'snapshot' of the tracer distribution at the time of image acquisition is acquired. There are diagnostic advantages to being able to measure the course of the tracer distribution over time (dynamic imaging).

The systems disclosed herein can have a small footprint and be used in a standard size mammography suite without requiring extensive reworking of existing mammography machines. Further, the systems can be useful in the clinical trial setting, as well as by oncology groups, pharmaceutical companies, etc to evaluate treatment effectiveness. The systems could further be useful in clinical practice to assess response to therapy for individual breast cancer patients to help select the optimal therapy for each patient. In several embodiments, the PET system can be portable and modular.

From the foregoing it will he appreciated that, although specific embodiments of the technology have been described herein for purposes of illustration, various modifications may be made without deviating from the spirit and scope of the technology. For example, the technology is described with reference to breast imaging, but can be used with other body parts (e.g., limbs, hands. or feet) or to scan small animals. Further, the technology can be used to detect or evaluate diseases other than cancer, such as arthritis or other diseases. Further, certain aspects of the new technology described in the context of particular embodiments may be combined or eliminated in other embodiments, Moreover, While advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A positron emission tomography (PET) system for use with a mammography machine, the system comprising:
   a tissue platform;
   a plurality of PET detection panels configured to be removably coupled to a mammography machine, wherein
   the plurality of PET detection panels is configured to completely surround the tissue platform about an axis parallel to the tissue platform; and
   a processing system configured to
      obtain, using the plurality of PET detection panels in a fixed state relative to tissue, an approximately 360-degree data sample of pairs of annihilation photons emitted indirectly by tracer introduced into the tissue, and
      reconstruct, using 360-degree data sample, an image displaying the tissue and an absolute quantity of tracer uptake within the tissue.

2. The PET system of claim 1 wherein the plurality of PET detection panels includes a top panel, a bottom panel, and two side panels.

3. The PET system of claim 2 wherein individual panels of the plurality of PET detection panels are movable and separable from one another.

4. The PET system of claim 1, further comprising a biopsy guidance grid configured for interchangeable placement with individual panels of the plurality of PET detection panels.

5. The PET system of claim 1 wherein the processing system is configured to obtain the 360-degree data sample to reconstruct the image displaying the tissue such that the image displaying the tissue has a spatial resolution of not larger than 4 mm.

6. The PET system of claim 1, further comprising the mammography machine, wherein the PET system is electrically integrated with the mammography machine, and wherein the processing system is further configured to obtain the data sample in combination with x-ray data of the tissue taken by the mammography machine.

7. The PET system of claim 1 wherein the processing system and the plurality of PET detection panels are further configured to obtain the 360-degree data sample as a function of time.

8. A method of using positron emission tomography (PET), the method comprising:
   removably coupling a plurality of PET detection panels to a mammography machine, wherein the plurality of PET detection panels is positioned to completely surround a tissue platform about an axis parallel to the tissue platform, and further wherein at least one panel is a bottom panel;
   obtaining a 360-degree data sample of tissue using the plurality of PET detection panels while the plurality of PET detections panels is in a fixed state relative to the tissue; and
   reconstructing, using the 360-degree data sample, an image displaying the tissue and an absolute quantity of tracer uptake within the tissue.

9. The method of claim 8, further comprising directing tissue sampling in response to the reconstructing.

10. The method of claim 8, further comprising quantifying radiotracer uptake in the tissue.

11. The method of claim 10, further comprising relating the absolute quantity of tracer uptake to an abnormality of the tissue.

12. The method of claim 8 wherein reconstructing the image comprises generating an image by combining the 360-degree data sample with x-ray data.

13. The method of claim 8 wherein reconstructing the image using the 360-degree data sample comprises generating an image having a spatial resolution of not larger than 4 mm.

14. The method of claim 8 wherein obtaining the 360-degree data sample of the tissue comprises dynamically acquiring a PET image as a function of time.

15. The method of claim 8 wherein obtaining the 360-degree data sample of the tissue comprises obtaining a baseline data sample, and wherein the method further comprises:
   implementing a treatment on a patient; and
   obtaining a post-therapy data sample.

16. The method of claim 8, further comprising correcting attenuation in data used to reconstruct the image through the use of x-ray mammography data.

* * * * *